US006683019B2

(12) United States Patent
Gartside et al.

(10) Patent No.: US 6,683,019 B2
(45) Date of Patent: Jan. 27, 2004

(54) CATALYST FOR THE METATHESIS OF OLEFIN(S)

(75) Inventors: Robert J. Gartside, Summit, NJ (US); Marvin I. Greene, Wayne, NJ (US); Ali M. Khonsari, Bloomfield, NJ (US); Lawrence L. Murrell, South Plainfield, NJ (US)

(73) Assignee: ABB Lummus Global Inc., Bloomfield, NJ (US)

( * ) Notice: Subject to any disclaimer, the term of this patent is extended or adjusted under 35 U.S.C. 154(b) by 0 days.

(21) Appl. No.: 09/880,670

(22) Filed: Jun. 13, 2001

(65) Prior Publication Data

US 2003/0028063 A1 Feb. 6, 2003

(51) Int. Cl.7 .......................... B01J 21/08; B01J 21/12; B01J 21/14
(52) U.S. Cl. .................. 502/241; 502/254; 502/255
(58) Field of Search ................... 502/241, 243, 502/250, 251, 252, 254, 255, 263, 407, 439; 501/54, 133

(56) References Cited

U.S. PATENT DOCUMENTS

| | | |
|---|---|---|
| 3,586,731 A | 6/1971 | Heckelsberg |
| 3,952,070 A | 4/1976 | Nowak et al. |
| 4,060,468 A | 11/1977 | Castner |
| 4,465,890 A | 8/1984 | Kukes et al. |
| 4,465,891 A | 8/1984 | Kukes et al. |
| 4,499,328 A | 2/1985 | Kukes et al. |
| 4,504,694 A | 3/1985 | Kukes et al. |
| 4,513,099 A | 4/1985 | Kukes et al. |
| 4,517,401 A | 5/1985 | Kukes et al. |
| 4,522,936 A | 6/1985 | Kukes et al. |
| 4,539,308 A | 9/1985 | Kukes et al. |
| 4,567,159 A | 1/1986 | Banks et al. |
| 4,575,575 A | 3/1986 | Drake et al. |
| 4,590,174 A | 5/1986 | Kukes et al. |
| 4,648,975 A * | 3/1987 | Barkatt et al. ............... 210/656 |
| 4,654,461 A | 3/1987 | Drake et al. |
| 4,681,956 A | 7/1987 | Schrock |
| 4,705,771 A * | 11/1987 | Spencer ..................... 502/255 |
| 4,727,215 A | 2/1988 | Schrock |
| 4,764,498 A * | 8/1988 | Wissner et al. ............. 502/251 |
| 4,795,734 A | 1/1989 | Chauvin et al. |
| 4,918,039 A | 4/1990 | Martin |
| 5,087,780 A | 2/1992 | Arganbright |
| 5,177,291 A | 1/1993 | Knuuttila et al. |
| 5,296,437 A | 3/1994 | Hietala et al. |
| 5,304,692 A | 4/1994 | Yamada et al. |
| 5,898,092 A | 4/1999 | Commereuc |
| 5,905,055 A | 5/1999 | Verdonck et al. |
| 5,942,653 A | 8/1999 | Du Plessis et al. |
| 5,962,363 A | 10/1999 | du Plessis et al. |
| 6,133,178 A * | 10/2000 | Yamada et al. ................ 501/54 |
| 6,136,736 A * | 10/2000 | Rajaram et al. ............... 501/54 |
| 6,153,546 A * | 11/2000 | Saitoh et al. .................. 501/37 |
| 6,156,692 A | 12/2000 | Nubel et al. |
| 6,159,890 A | 12/2000 | Nubel et al. |
| 6,175,047 B1 | 1/2001 | Hori et al. |
| 6,235,669 B1 * | 5/2001 | Antczak et al. ............. 501/133 |
| 6,296,826 B1 * | 10/2001 | Fujinoki et al. ............. 423/335 |
| 6,451,719 B1 * | 9/2002 | Yamagata ..................... 501/54 |
| 6,482,324 B2 * | 11/2002 | Kirkland et al. ............. 210/656 |

FOREIGN PATENT DOCUMENTS

| | | |
|---|---|---|
| DD | 137 923 | 10/1979 |
| WO | WO 02/059066 A1 | 8/2002 |

* cited by examiner

*Primary Examiner*—Cam N. Nguyen
(74) *Attorney, Agent, or Firm*—Dilworth & Barrese, LLP

(57) ABSTRACT

An olefin metathesis catalyst consists essentially of a transition metal or oxide thereof supported on a high purity silica support possessing low amounts of acidic or basic sites such that in the reaction of pure butene-1 over said catalyst under metathesis reaction conditions the reaction possesses a weight selectivity to hexene-3 of at least 55 wt %.

6 Claims, No Drawings

CATALYST FOR THE METATHESIS OF OLEFIN(S)

BACKGROUND OF THE INVENTION

1. Field of the Invention

The present invention relates to a supported catalyst for the metathesis, or disproportionation, of olefin(s), and to a metathesis process employing the catalyst.

2. Description of the Related Art

The metathesis, or disproportionation, of olefin(s) is a reaction in which one or more olefinic compounds are transformed into other olefins of different molecular weights. The disproportionation of an olefin with itself to produce an olefin of a higher molecular weight and an olefin of a lower molecular weight is also referred to as self-disproportionation. For example, propylene can be disproportionated to ethylene and cis- and trans-2-butene. Another type of disproportionation involves the cross-disproportionation of two different olefins to form still other olefins. An example would be the reaction of one molecule of 2-butene with one molecule of 3-hexene to produce two molecules of 2-pentene.

When olefins are contacted with metathesis catalysts, the reactions proceed according to a specific structural relationship depending upon the character of the feedstock. The reaction is generally considered to proceed using a four-centered active site on the catalyst. The olefinic double bonds line up on opposite sides of the four-centered site. The reaction proceeds under equilibrium conditions with the bonds exchanging sides of the four-centered site and thusly exchanging the hydrocarbon groups attached to one end of the double bond with the groups attached to the other olefin. For example, 2-butene if reacted with ethylene can form two propylene molecules as shown by equation (1) where each corner of each box in equation (1) represents one of the four active sites on the catalyst:

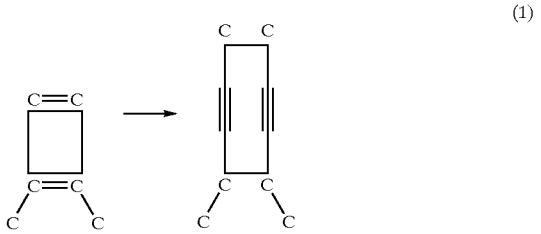

(1)

Extending this concept to any number of olefins, one can see that depending upon the nature of the R group attached to the double bonds, different olefins are formed with strict adherence to the exchange of R groups around the double bond. Thus, olefin R1-C=C—R2 when reacted with olefin R3-C=C—R4 forms an olefin of R1-C=C—R3 and an olefin of R2-C=C=—R4 This is illustrated in equation (2) where each corner of each box in equation (2) represents one of the four active sites on the catalyst:

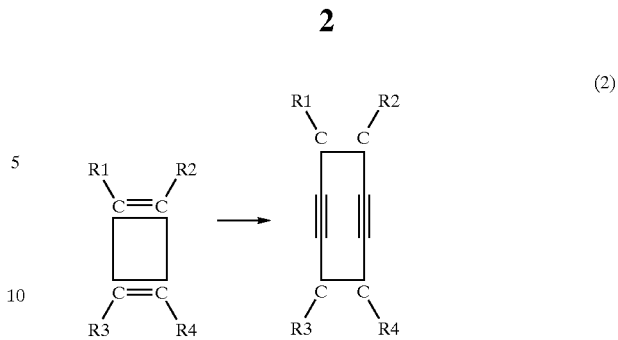

(2)

One skilled in the art can imagine many potential reactions over the entire range of possible olefin pairs.

In addition to the metathesis reactions, however, it is not uncommon for various side reactions to occur. One such reaction is an oligomerization reaction where olefins combine to form larger olefins. This reaction, if the olefin grows large enough, leads to fouling of the catalyst as the active sites are blocked. Another reaction that could occur is the double bond isomerization of the olefin. In this case, the position of the double bond shifts within the hydrocarbon chain. Examples are the isomerization of 1-butene to 2-butene and 3-hexene to 2-hexene. If this occurs, the number and character of the olefins available for metathesis changes. With olefins having different R groups available, different reaction products can be formed. The isomerization side reaction leads to a loss in the selectivity of the metathesis reaction to the products defined by the structure of the feedstock olefins.

For example, if the feedstock to the metathesis reaction was essentially pure 1-butene, the primary products of that reaction would be ethylene and 3-hexene. No other products would form. If, however, some portion of the 1-butene was isomerized to 2-butene, then 1-butene could react with 2-butene to form propylene and 2-pentene. The propylene and pentene represent non-selective products.

The ability to control unwanted side reactions allows the process designer to selectively produce specific products based upon the purity and character of the feedstocks. In many cases this is important to maximize the value of a particular reaction. An example of such a process where selectivity is critical is the production of linear alpha olefins as described in commonly assigned, co-pending U.S. patent application No. 60/263,924, filed Jan. 25, 2001, incorporated by reference herein. That process requires a catalyst with low isomerization activity as described therein.

Many catalysts have been developed for metathesis. For example, those comprising inorganic oxides containing a catalytic amount of a metal or metal oxide have been employed widely for continuous, fixed-bed conversion of olefins. One such catalyst comprises a silica support and an oxide of tungsten. The present invention is based on the discovery of a way to improve the selectivity of metathesis catalysts to specific products.

SUMMARY OF THE INVENTION

In accordance with the present invention, a metathesis catalyst is provided which consists essentially of a transition metal or oxide thereof supported on a high purity silica support. "High purity silica" is defined as silica possessing low amounts of acidic or basic sites such that in a reaction of pure 1-butene over said catalyst under metathesis conditions the reaction possesses a weight selectivity to hexene-3 of at least 55 wt %. Specifically, the high purity silica support contains less than about 150 ppm magnesium, less than about 900 ppm calcium, less than about 900 ppm sodium, less than about 200 ppm aluminum and less than about 40 ppm iron.

A critical feature of the catalyst of this invention is the purity of the silica support. Certain impurities adversely affect the activity and selectivity of metathesis catalysts. Activity-affecting and selectivity-affecting impurities such as aluminum and iron form acidic sites that will act as sites for olefin isomerization. Alkali metal impurities such as sodium and alkaline earth metal impurities such as calcium and magnesium form basic sites that also act as double bond isomerization catalysts at temperatures employed in metathesis reactions. The amounts of activity-affecting impurities in the catalyst of the invention are substantially below the amounts of such impurities present in conventional silica supports currently employed in the preparation of metathesis catalysts. As a result, the catalyst of the invention exhibits superior selectivities to the desired metathesis reaction products, and minimizes the production of undesired double bond isomerization reaction products.

The lower impurities levels of the catalysts of this invention also lead to a more environmentally friendly catalyst in which the trace elements leachability rates upon landfilling of the fully spent catalysts will be lower than those of the commercial silica formulations.

DETAILED DESCRIPTION OF THE PREFERRED EMBODIMENTS

The high purity silica support utilized in the preparation of the metathesis catalyst of the invention possesses low amounts of both acidic and basic sites (preferably essentially no acidic and basic sites) and thereby improves the selectivity of the metathesis reaction and minimizes undesirable double bond isomerization.

By "low amount" of acidic and basic sites on the support, it is meant that the silica support possesses less than about 150 ppm magnesium (measured as the element), less than about 900 ppm calcium (measured as the element), less than about 900 ppm sodium (measured as the element), less than about 200 ppm aluminum (measured as the element) and less than about 40 ppm iron (measured as the element). Preferably, the high purity support possesses less than about 100 ppm magnesium, less than about 500 ppm calcium, less than about 500 ppm sodium, less than about 150 ppm aluminum and less than about 30 ppm iron. More preferably, the high purity support possesses less than about 75 ppm magnesium, less than about 300 ppm calcium, less than about 300 ppm sodium, less than about 100 ppm aluminum and less than about 20 ppm iron. High purity silica within the scope of this invention can be commercially obtained as chromatographic grade silica.

Transition metals and oxides thereof that can be employed herein are known and include, but are not limited to, tungsten, molybdenum, rhenium, oxides thereof and mixtures thereof. Tungsten oxide is particularly preferred. The oxides of these metals are typically formed from oxide precursors which are subsequently converted to the oxides by calcination. Suitable precursors include compounds which are convertible to the oxide form under calcination, such as, for example, the halides, oxides, sulfides, sulfates, nitrates, acetates, ammonium salts, and the like, and mixtures of any two or more thereof. Ammonium meta tungstate is preferably utilized as the precursor for the tungsten deposited upon the high purity support.

The transition metal or oxide thereof is deposited on the high purity support material in an amount that varies between 1 and 20% by weight, based on the weight of the entire catalyst.

The metathesis catalyst utilized herein should not be intentionally admixed with double bond isomerization catalysts, including supported or unsupported phosphoric acid, bauxite, zinc oxide, magnesium oxide, calcium oxide, cerium oxide, thorium oxide, titanium oxide, cobalt oxide, iron oxide, or manganese oxide, and the like, since such isomerization catalysts will significantly interfere with the desired metathesis reaction.

The high purity silica support and transition metal or oxide thereof can be contacted in any suitable manner. For example, the support and a solution containing the transition metal or oxide thereof (or precursor thereof) (hereinafter referred to simply as the transition metal) can be mixed in an open vessel, then any excess liquid can be decanted or removed by filtration. Alternatively, the technique of incipient wetness can be employed whereby only enough liquid is employed to thoroughly wet the support, with no free residual liquid. Thus, only as much transition metal-containing solution is employed as the support can absorb. This can be accomplished, for example, by spraying the solution over a quantity of support which is being tumbled in a rotating, baffled drum. Such treatment can also be carried out by simply pouring a predetermined quantity of the solution over a quantity of the silica support in an open vessel. Alternatively, a measured quantity of support could be added to a volume of transition metal-containing solution such that all of the liquid is imbibed by the added support. Other techniques are known to those skilled in the art and can also be employed. For example, a quantity of support may be placed in a tubular reactor, a volume of transition metal-containing solution may be percolated there through, followed by further treatment/activation as necessary.

The conditions of high purity silica support/transition metal-containing solution contacting are not critical. Any temperature and any period of contact time are suitable. For convenience, contacting is generally carried out at about room temperature, although higher or lower temperatures can be employed. A time period sufficient to allow the support and reagents to come into intimate contact is all that is necessary. Thus, the support and solution may be brought into contact for as little time as a few seconds to several hours or more, as convenient.

Following contact of the high purity silica support and transition metal-containing solution, any excess liquid can be removed by suitable means, such as, for example, decantation, filtration or the like. The treated support can be dried to removed absorbed solvent. Any suitable means, as well known by those skilled in the art, may be employed such as, for example, oven drying, passing a vigorous stream of dry (moisture-free) gas over the treated support and the like. For example, the supported catalyst can be dried by heating at an elevated temperature of, e.g., about 200° C. or higher by passage of an inert gas such as nitrogen over the material. This can be accomplished within the reactor or in other suitable catalyst preparation equipment.

Calcination, when used, is conducted by heating the transition metal oxide or precursor thereof in the presence of an oxygen-containing gas, such as, for example, air, under conditions sufficient to activate the metal oxide, e.g., tungsten oxide, or to convert the transition metal compound present, e.g., tungsten, to the activated metal oxide form. Temperatures in the range of about 350° C. to about 800° C. are generally satisfactory for such calcinations. The time for subjecting the transition metal oxide to calcination is an amount of time sufficient to activate the catalyst. Anywhere from a few minutes to several hours is suitable. Typically, about 15 minutes to about 20 hours of calcination will be sufficient. Preferably, for the most efficient use of reaction equipment, the transition metal oxide will be subjected to calcination for about 30 minutes to about 6 hours at temperatures less than 650° C. Higher temperatures while acceptable can result in loss of support surface area and reduction in catalyst activity. Typically less time is required at higher temperatures and vice versa.

After calcination, the metathesis catalyst is optionally treated under reducing conditions such as, for example, with carbon monoxide, hydrogen, or a hydrocarbon at a temperature in the range of from about 350° C. to about 550° C. to enhance the metathesis activity of the catalyst. Such reducing treatment is carried out preferably in the range of from about 400° C. to about 450° C., because good catalyst activation with relatively short activation periods of about one to about six hours can be achieved. Such optional reducing treatment can suitably be carried out for a period of time ranging from about 1 minute to about 30 hours. If desired, the calcined catalyst can be further treated with an inert gas such as nitrogen prior to use in a metathesis reaction to remove adsorbed materials from the catalyst which may have a detrimental effect on the selectivity of the catalyst for metathesis reactions. Such materials are water or $CO_2$ that could be adsorbed by the catalyst through contact with the ambient environment.

Further in accordance with the invention, a process is provided in which one or more olefins capable of undergoing a metathesis reaction are contacted with the catalyst of the invention under metathesis reaction conditions which minimize or eliminate double bond isomerization reactions to provide a metathesis reaction product. In particular, such catalyst and conditions are selected such that in a reaction of pure butene-1 over said catalyst under metathesis reaction conditions the reaction possesses a weight selectivity to hexene-3 of at least 55%, and preferably at least 60% or greater.

Olefins employed in the practice of the process of the invention will generally possess up to about 30 carbon atoms, preferably from about 3 to about 25 carbon atoms, and more preferably from about 4 to about 18 carbon atoms. Some specific examples of olefins which may be employed are propylene, 1-butene, 2-butene, 1-pentene, 2-pentene, 2,4,4-trimethyl-2-pentene, 2,4,4-trimethyl-1-pentene, 1-hexene, 2-heptene, 1-octene, 2-nonene, 1-dodecene, 2-tetradecene, 1-hexadecene, 1-phenyl-2-butene, 4-octene, 3-eicosene, 3-hexene, 2-methy-4-octene, 1,5,9,13,17-octadecapentene, 8-cyclopentyl-4,5-dimetyl-1-decene, 3-heptene, and the like, and mixtures thereof.

The metathesis reaction conditions in accordance with the invention include a temperature of from about 50° C. to about 600° C., preferably from about 200° C. to about 400° C., a weight hourly space velocity (WHSV) of from about 3 to about 200, preferably from about 6 to about 40, and a pressure of from about 10 psig to about 600 psig, preferably from about 30 psig to about 100 psig. The reaction may be carried out by contacting the olefin(s) with the catalyst in the liquid phase or the gas phase depending on structure and molecular weight of the olefin(s). If the reaction is carried out in the liquid phase, solvents or diluents for the reaction can be used. Aliphatic saturated hydrocarbons, e.g., pentanes, hexanes, cyclohexanes, dodecanes and aromatic hydrocarbons such as benzene and toluene are suitable. If the reaction is carried out in the gaseous phase, diluents such as saturated aliphatic hydrocarbons, for example, methane, ethane, and/or substantially inert gases, e.g., nitrogen, argon, can be present. Preferably, for high product yield, the reaction is conducted in the absence of significant amounts of deactivating materials such as water and oxygen.

The contact time needed to obtain a desirable yield of metathesis reaction products depends upon several factors such as the activity of the catalyst, temperature, pressure, and the structure of the olefin(s) to be metathesized. Length of time during which the olefin(s) are contacted with catalyst can conveniently vary between 0.1 seconds and 4 hours, preferably from about 0.5 sec to about 0.5 hrs.

The process can be conducted batch-wise or continuously with fixed catalyst beds, slurried catalyst, fluidized beds, or by using any other conventional contacting techniques.

In accordance with a preferred embodiment of the present invention, butene-1 is contacted with the catalyst of the invention and reacted under metathesis reaction conditions under conditions that minimize isomerization of the butene-1 to produce a reaction product that includes ethylene and hexene-3. The reaction is:

$$1\text{-}C_4^= + 1\text{-}C_4^= \rightarrow C_2^= + 3\text{-}C_6^=$$

The butene-1 starting material may be a pure or impure feed. The portion of the feed that contains reactive $C_4$ olefins is preferably at least 90% and more preferably at least 95% butene-1. Non-reactive components, for example normal butane, may dilute the olefins in the feedstock. Most preferably, the butene-1 starting material is a pure feed, i.e., the butene-1 is present in an amount of at least 99%.

The invention now will be described with respect to the following examples; however, the scope of the present invention is not intended to be limited thereby.

EXAMPLE 1

In this example, a catalyst containing 5% by weight $WO_3$ on a high purity silica support was produced via the incipient wetness technique using ammonium meta-tungstate. 20.5 gm of the high purity silica support was dried in an air atmosphere in an oven at 300° C. for 20 hrs. The sample lost 6 weight percent moisture. A solution of ammonium meta-tungstate, 2938 molecular weight, was prepared by dissolving 1056 mg of the meta-tungstate in 20 cc distilled water. The resultant salt solution was added dropwise to the dried high purity silica support with gentle mixing between the dropwise addition steps. The resultant mix of the 20 cc salt solution and the dried high purity silica was dried in an air atmosphere in an oven at 115° C. for 2 hours. This was followed by calcination in an air atmosphere in a high temperature oven at 500° C. for 2 hours using a temperature ramping rate of 2° C./min. At the end of the 2 hrs, the oven was de-energized and the calcined catalyst was cooled to room temperature in an air atmosphere.

The high purity support was analyzed for impurities and compared to the impurities of samples of other available silica supports. Samples A through F are random samples from a single batch of a commercially available silica support available from Engelhard Corporation designated L6700-450. There is a wide variation in the impurity levels even within a commercial batch. The high purity silica is a chromatographic grade silica from Zeolyst International designated CS-1030. Table 1 compares the impurity ranges.

TABLE 1

| Support | Mg (ppm) | Ca (ppm) | Na (ppm) | Al (ppm) | Fe (ppm) |
|---|---|---|---|---|---|
| Sample A | 321 | 1619 | 982 | 245 | 30 |
| Sample B | 324 | 1655 | 1456 | 278 | 56 |

TABLE 1-continued

| Support | Mg (ppm) | Ca (ppm) | Na (ppm) | Al (ppm) | Fe (ppm) |
|---|---|---|---|---|---|
| Sample C | 83 | 519 | 1233 | 269 | 86 |
| Sample D | 58 | 356 | 764 | 283 | 41 |
| Sample E | 322 | 1637 | 1219 | 262 | 43 |
| Sample F | 70 | 438 | 998 | 276 | 64 |
| Average | 196 | 1037 | 1108 | 269 | 53 |
| High Purity Silica | 55 | 95 | 147 | <100 | <10 |

It can readily be seen that the high purity support contains substantially lower amounts of impurities compared to Samples A through F.

EXAMPLE 2

Pure butene-1 was passed over a catalyst consisting essentially of a high purity support-impregnated by $WO_3$ and, separately, over a catalyst containing a mixture of commercial silica supports A through F impregnated by $WO_3$ at a WHSV of 14 wt feed olefins/hr-wt catalyst and at a pressure of 75 psig. The reaction temperature was 343° C. over the catalyst. Molar selectivity is calculated by dividing the moles of each product by the moles of butene-1 converted to all products. The selectivities to various components are given in Table 2 below.

TABLE 2

Effect of Catalyst Support on Butene-1 -Self-Disproportionation

| | $WO_3$ on lower purity commercial support Selectivity | | $WO_3$ on high purity silica support Selectivity | |
|---|---|---|---|---|
| Selectivity to: | Molar | Weight | Molar | Weight |
| Ethylene | 36.6 | | 44.1 | |
| Hexene-3 | 36.8 | 53.2 | 45.1 | 65.3 |
| Ethylene + Hexene-3 | 73.4 | | 89.2 | |
| Propylene | 12.8 | | 4.8 | |
| Pentene-2 | 11.8 | | 4.3 | |
| Propylene +Pentene-2 | 24.6 | | 9.1 | |
| Heptenes+ | 2.0 | | 0.2 | |
| Butene-2 | 0 | | 1.2 | |
| n-Butenes Conversion | 49.7 | | 40.7 | |
| Butene-1 Conversion | 50.2 | | 41.1 | |

As shown in Table 2 above, there is considerable unexpected improvement in performance associated with the high purity catalyst support compared to a low purity catalyst support. Although not wishing to be bound by theory, this is probably the result of fewer acidic sites due to lower aluminum content and fewer basic sites due to the significantly lower amounts of calcium and magnesium impurities. The effect of the impurity levels is magnified as a result of operation within the reactor. Exposure to high temperatures and oxidation/reduction conditions results in the migration of impurities from the bulk phase of a support to the surface. In samples of $WO_3$ catalyst supported on commercial silica, Mg on the surface has been shown to increase by a factor of 3 or more. Accordingly, by reducing the amount of bulk impurities present in the support, catalytic selectivity is significantly enhanced.

It is to be understoodthat the scope of the present invention is not to be limited to the specific embodiments described above. The invention may be practiced other than as particularly described and still be within the scope of the accompanying claims.

What is claimed is:

1. A metathesis catalyst consisting essentially of a transition metal or oxide thereof supported on a high purity silica support, said high purity silica support possessing low amounts of acidic or basic sites such that in a reaction of pure 1-butene over said catalyst under metathesis reaction conditions the reaction possesses a weight selectivity to hexene-3 of at least 55 weight percent, wherein the high purity silica support possesses less than about 150 ppm magnesium, less than about 900 ppm calcium, less than about 900 ppm sodium, less than about 200 ppm aluminum and less than about 40 ppm iron.

2. The catalyst of claim 1 wherein the high purity silica is chromatographic grade silica.

3. The catalyst of claim 1 wherein the weight selectivity to hexene-3 is greater than 60 weight percent.

4. The catalyst of claim 1 wherein the transition metal or oxide thereof represents from about 1 to about 20 weight percent of the catalyst.

5. The catalyst of claim 1 wherein the transition metal or oxide thereof is selected from the group consisting of tungsten, molybdenum, rhenium, and mixtures thereof.

6. The catalyst of claim 1 wherein the transition metal or oxide thereof is tungsten or tungsten oxide.

* * * * *